United States Patent
Canda (10) Patent No.: US 10,380,740 B2
(45) Date of Patent: Aug. 13, 2019

(54) DETERMINATION OF AN IMAGE SERIES IN DEPENDENCE ON A SIGNATURE SET

(71) Applicant: Siemens Healthcare GmbH, Erlangen (DE)

(72) Inventor: Valer Canda, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 74 days.

(21) Appl. No.: 15/650,049

(22) Filed: Jul. 14, 2017

(65) Prior Publication Data

US 2018/0018773 A1     Jan. 18, 2018

(30) Foreign Application Priority Data

Jul. 14, 2016 (DE) .................. 10 2016 212 888

(51) Int. Cl.
| | |
|---|---|
| *G06T 7/00* | (2017.01) |
| *G06T 7/10* | (2017.01) |
| *G16H 40/63* | (2018.01) |
| *G06T 7/136* | (2017.01) |
| *G06T 7/174* | (2017.01) |
| *G16H 30/20* | (2018.01) |
| *G06K 9/00* | (2006.01) |

(52) U.S. Cl.
CPC ............. *G06T 7/10* (2017.01); *G06T 7/136* (2017.01); *G06T 7/174* (2017.01); *G06T 7/97* (2017.01); *G16H 30/20* (2018.01); *G16H 40/63* (2018.01); *G06K 2009/00489* (2013.01); *G06T 2207/10088* (2013.01)

(58) Field of Classification Search
CPC .......... G06T 7/10; G06T 7/136; G06T 7/174; G06T 7/97; G06T 2207/10088; G16H 30/20; G16H 40/63; G06F 19/00; G06K 2009/00489
See application file for complete search history.

(56) References Cited

U.S. PATENT DOCUMENTS

| | | | |
|---|---|---|---|
| 5,870,754 A | 2/1999 | Dimitrova et al. | |
| 8,094,901 B1 | 1/2012 | Reicher et al. | |
| 8,976,190 B1 | 3/2015 | Westerhoff et al. | |
| 2005/0152588 A1* | 7/2005 | Yoshida ................ | G06T 7/0012 382/128 |
| 2007/0253609 A1* | 11/2007 | Aben ....................... | G06T 7/11 382/128 |

(Continued)

OTHER PUBLICATIONS

Wang et al., "Intelligent Tools for a Productive Radiologist Workflow: How Machine Learning Enriches Hanging Protocols," GE Healthcare, pp. 1-8 (2013).

(Continued)

*Primary Examiner* — John W Lee
(74) *Attorney, Agent, or Firm* — Schiff Hardin LLP (57) ABSTRACT

For the determination of an image series from a set of a number of image series, in each case of a signature is compiled for each of the number of image series. This signature is formed from a set of attributes of the respective image series. A signature from the signatures for the image series is ascertained that is most similar to a prespecified signature set. An action is performed with the image series whose signature was ascertained as the most similar signature.

14 Claims, 3 Drawing Sheets

(56) References Cited

U.S. PATENT DOCUMENTS

| | | | |
|---|---|---|---|
| 2009/0297048 A1* | 12/2009 | Slotine | G06K 9/4671 |
| | | | 382/224 |
| 2010/0160765 A1* | 6/2010 | Marrouche | G06T 7/0012 |
| | | | 600/410 |
| 2010/0232661 A1 | 9/2010 | Hisanaga et al. | |
| 2010/0239144 A1* | 9/2010 | Fichtinger | A61B 5/415 |
| | | | 382/131 |
| 2010/0306193 A1 | 12/2010 | Pereira et al. | |
| 2012/0041277 A1* | 2/2012 | Ebadollahi | A61B 5/0205 |
| | | | 600/301 |
| 2012/0063655 A1* | 3/2012 | Dean | G06F 19/321 |
| | | | 382/128 |
| 2012/0189176 A1* | 7/2012 | Giger | G06K 9/6253 |
| | | | 382/128 |
| 2013/0129198 A1 | 5/2013 | Sherman et al. | |
| 2014/0003695 A1* | 1/2014 | Dean | G06T 7/0012 |
| | | | 382/131 |
| 2014/0099023 A1 | 4/2014 | Lo et al. | |
| 2015/0154356 A1* | 6/2015 | Alvarez Del Castillo | |
| | | | G16H 30/20 |
| | | | 715/853 |
| 2015/0161147 A1 | 6/2015 | Zhao et al. | |
| 2015/0199428 A1 | 7/2015 | Jia et al. | |
| 2015/0205821 A1 | 7/2015 | Kogan | |
| 2015/0254493 A1* | 9/2015 | Madabhushi | G06K 9/0014 |
| | | | 382/133 |
| 2016/0203599 A1* | 7/2016 | Gillies | A61B 6/463 |
| | | | 382/132 |
| 2016/0267179 A1 | 9/2016 | Mei et al. | |

OTHER PUBLICATIONS

Siemens Healtheniers, "Syngo.via for MRI," healthcare.siemens.de/magnetic-resonance-imaging/advanced-imaging-applications/syngo-via/use (2016).

Asbach et al., "Efficient Whole-Body MRI Interpretation: Evaluation of a Dedicated Software Prototype," Journal of Digital Imaging, vol. 21, Suppl. 1, pp. S50-S58 (2008).

Müller-Horvat et al., "Generating Statements at Whole-Body Imaging with a Workflow-Optimized Software Tool—First Experiences with Multireader Analysis," Fortschr. Röntgenstr., vol. 179, pp. 721-727 (2007).

European Search Report dated Dec. 14, 2017—Application No. EP 17 174931.0, and English language translation attached.

European Office Action dated Apr. 24, 2018—Application No. 17 174 931.0, and English language translation attached.

Communication under Rule 71(3) EPC—Intent to Grant, dated Jun. 27, 2018, and English language translation attached.

\* cited by examiner

FIG 1

DETERMINATION OF AN IMAGE SERIES IN DEPENDENCE ON A SIGNATURE SET

BACKGROUND OF THE INVENTION

Field of the Invention

The present invention concerns the determination of an image series from a set of image series in dependence on a signature set. The present invention in particular concerns the determination of images, which are created by an imaging system, in order to depict these images and to use these images to be able to perform a radiological evaluation.

Description of the Prior Art

For example, a workflow-based approach has been found to be efficient for the assessment of complex MR data sets in order to enable the fastest possible evaluation of MR images created using the MR data sets. In this context, the MR images are depicted in a layout on a display, the layout having a number of segments. An MR image or an MR image series is depicted in each of these segments.

In this context, (if present) an MR image or an MR image series corresponding to a specific part or organ system of the patient to be examined is depicted in each segment. For example, an MR image series of the patient's skeletal system can be depicted in one segment, while an MR image series of the thorax or the pelvis or specific organs of the patient is depicted in other segments. As a further possibility, the segments can differ with respect to image contrast or with respect to alignment or with respect to a phase property. If it is possible for a number of different image series to be depicted for a segment, the image series displayed is the one most appropriate for the current evaluation.

SUMMARY OF THE INVENTION

An object of the present invention is to improve the image series to be depicted in a specific segment of the layout compared to the prior art.

The present invention provides a method for the determination of an image series from a set of a number of image series, with the following steps.

A signature is compiled for each of the number of image series, with this signature being formed from a set of attributes of the respective image series. In this step, the attribute or attributes of the respective signature is/are formed from the attributes of the associated image series. To this end, it is possible for specific attributes of the image series to be adopted as an attribute of the signature, for attributes of the image series to be linked in order in this way to determine an attribute of the signature, or for an attribute of the signature to be derived in another way from the attributes of the image series.

A signature is ascertained from the signatures of the image series that is most similar to a prespecified signature set. In this step, the image series ascertained from the set with reference to the signatures is the signature (and hence image series) with the greatest similarity to the prespecified signature set.

An action is performed with the image series from the set of image series whose signature was ascertained in the preceding step as the most similar signature.

The method according to the invention enables the determination from a set of image series of the image series that best satisfies a prespecified condition. Since the measure for the satisfaction of the prespecified condition is translated into a degree of similarity between a signature and a signature set describing the condition, the present invention offers a simple procedure that can be adapted to numerous conditions for the automatic determination of the best matching image series.

The present invention can be used in order to determine which image series from a set of image series is most suitable to be displayed in a specific segment of a layout. In addition, in particular the following procedures (also combinable) are provided with which the present invention can be used:

Image Evaluation

The present invention can be used to select the image series from a set of image series that is most suitable for a medical image evaluation. In this context, the medical image evaluation can, for example, comprise the ascertainment of the dimensions of an organ of the examination object.

Depiction

The present invention can be used to select the image series from a set of image series that is most suitable for depiction in an assessment report and/or on a filming sheet and hence for the assessment or confirmation of a specific condition for example of a patient. In this context, a filming sheet or film sheet should be understood to be a type of transparent film on which a specific image or a plurality of specific images of the image series are applied (for example printed) in order, for example, to be viewed in front of a light box. However, a filming sheet can also be part of the assessment report.

Image Post-Processing

The present invention can be used to select the image series from a set of image series that is most suitable for image post-processing. Image post-processing comprises, for example, the calculation of a perfusion map, the calculation of subtraction series or the performance of motion correction for the one or more image series selected. The image post-processing generally includes the calculation of one or more new image series on the basis of one or more original image series.

Forwarding

The present invention can be used to select the image series from a set of image series that is most suitable for automatic forwarding for example to other systems (for example PACS ("Picture Archiving and Communication system")). For example, it is possible to ascertain the image series for forwarding that best depicts a specific region of the examination object with which the reception system (or the operator of the reception system) is specifically concerned.

Archiving

The present invention can be used to select the image series from a set of image series that is most suitable for automatic archiving. For example, according to the invention it is possible to archive precisely the image series that is most suitable to confirm a specific assessment.

Discarding

The present invention can be used to select the image series from a set of image series that is most likely not suitable for another action (in particular not suitable for one of the above-described actions).

In one variant, it is possible for a degree of similarity to be defined that indicates a similarity between the signature and the signature set. It is then possible for all image series with which the degree of similarity between the respective signature of the image series and the signature set is above a predetermined similarity threshold to be discarded.

For example, it is possible to discard image series used, for example, to localize specific slices inside the examination object so that only image series required for the assessment are forwarded or archived.

According to the invention, it is possible to combine the discarding according to the invention with one of the other above-described procedures. In the case of such a combination, the other procedure can be carried out for each of the image series that was not discarded. In other words, the respective procedure (i.e. the image evaluation, the depiction, the image post-processing, the forwarding and/or the archiving) is carried out for each of the image series that was not discarded without the respective non-discarded image series additionally having to be most suitable for the respective procedure.

A method is also provided by the present invention for the determination of images created with the use of an imaging system images for evaluation by an operator. This method has the following steps.

A layout is created with a number of segments in order to depict this layout on a display. The layout to be depicted or the content of the display is accordingly divided into a plurality of segments.

A respective signature set or collection of signatures is assigned to each segment. In this step, one or more signatures which are combined in a respective signature set are assigned to each segment. In this context, each signature is formed from a set of at least one attribute (but usually multiple attributes) of an image series. In this context, an image series should be understood to be an ordered set of one image, or generally a plurality of images. The signature set for each segment can be expanded, reduced or changed.

In each case a signature is compiled for a number of image series. In this step, a signature is compiled for each image series for a number of image series, which was compiled with the imaging system.

A signature from the signatures of the image series is assigned that is most similar to the signature set of the respective segment. In this step, one of the signatures of the image series is ascertained for each of the segments. In this context, the signature ascertained for the respective segment is the signature of the image series with the greatest similarity to the signature set of the respective segment.

The image series in the respective segment is depicted whose signature was ascertained in the step of the ascertainment of the signature for each of the segments as the most similar signature. In this step, an image series is depicted for each segment of the layout. In this context, the image series depicted for each segment corresponds to the image series whose signature was ascertained as the most similar signature for the respective segment (to be more precise, for the signature set of the respective segment).

Contrary to the prior art according to which, for example, a specific designation of an image series or specific conditions for the image series to be depicted are indicated for each segment, according to the invention, it is only necessary in accordance with the invention for the corresponding signature set to be defined for each segment. In this context, a signature of this signature set can, for example, be compiled with reference to a previously compiled exemplary image series.

The attributes of a signature can each have, for example:
a name,
a data type, for example integer, floating-point number, date, string, UDI (i.e. a sequence of digits and points), binary sequence, etc.
one or more pieces of data of the respective type. An attribute can contain only one data value of the respective data type, i.e. only one floating-point number or only one string. However, it is also possible for an attribute to comprise, for example, a plurality of data values, for example three floating-point numbers, wherein these three floating-point numbers can be interpreted as a 3D vector indicating a position in space (for example spatial coordinates [x, y, z] in centimeters).

The above-described step of the ascertainment of the most similar signature can include determination for all image series of a distance or spacing between the signature of the respective image series and the signature set. In this substep, the distance between its signature and the signature set is ascertained for each image series. The ascertainment also includes determination of the most similar signature as the signature with the shortest distance to the signature set.

Since a distance to the signature set of a specific segment is automatically determined for all signatures of the image series and then the signature ascertained as the most similar signature is that with the shortest distance to the signature set, the determination of the image series to be depicted in the specific segment can be very effectively automated.

However, it is also possible according to the invention to determine the signature from the set of signatures of all image series with the shortest distance to the signature set of a specific segment without this requiring the distance between the signature of each image series and the signature set of the specific segment having to be determined.

Depending upon how the distance between a signature and a signature set is defined, it is, for example, possible to use specific properties of the signature to check preconditions that have to be satisfied so that a specific signature has a shorter distance to the signature set than another signature. Checking such preconditions enables the explicit determination of the distance to the signature set for numerous signatures to be advantageously avoided.

The distance between a signature and a signature set can be determined using one of the following possibilities according to the invention. In this context, with each of these possibilities, the distance between the signature and the signature set is determined in dependence on distances between the signature and each signature of the signature set.

With the first possibility, the distance between the signature and the signature set is determined as the distance that is the shortest distance from the set of distances between the signature and each signature of the signature set.

With the second possibility, the distance between the signature and the signature set corresponds to the mean value of the distances between the signature and each signature of the signature set.

With the third possibility, the distance between the signature and the signature set is determined as a weighted sum of the distances between the signature and each signature of the signature set. In this context, the weighting of the signatures in the signature set can be reduced depending on the position thereof in the signature set. For example, the position of the respective signature in the signature set can depend upon the date of compilation of the signature (or the time at which the signature was attached to the signature set). This would ensure that, the newer the signatures in the signature set, the greater the weighting assigned to the signature (and hence the associated image series).

According to the above-described possibilities according to the invention, the determination of the distance between a signature and a signature set is so-to-speak performed using the determination of a number of distances between two signatures in each case. In this context, the distance between two signatures can be determined in dependence on the distances with corresponding attributes of the two signatures with respect to each other.

It is possible for all signatures have the same attributes.

Occasionally, it happens that specific attributes of an image series are not set. Depending on the manner in which the attributes of the signature are formed on the basis of the attributes of the image series, it is then also possible for one attribute or a number of attributes of the associated signature not to be set, i.e. to have the value 0 or " " or N/A ("not available"). This means that when a signature has an attribute, the value of this attribute can be set or not set.

Let it be assumed that the attributes of each signature are sorted in the same way so that the n-th signature of each signature describes the same type and the sort of attribute. In order now to determine the distance between two signatures, in a first step, the distance between the first attributes of the two signatures, the distance between the second attributes of the two signatures, etc. is ascertained. In a second step, the distance values for the individual attributes are either simply added up or first weighted and then added up. In other words, the distance between two signatures in particular corresponds to the sum of the distances of the individual attributes of the two signatures, wherein the distances of the individual attributes can in each case be weighted as can be derived from the following equation (1).

$$D(Sig1, Sig2) = \sum_{i=1}^{N} G_i \times DistAttr(Sig1 \cdot Attr(i), Sig2 \cdot Attr(i)) \quad (1)$$

In this context:

$D(Sig1, Sig2)$ is the distance to be calculated between the two signatures $Sig1$ and $Sig2$;

N is the number of attributes of the two signatures;

$DistAttr()$ is a function with which the distance between two attributes is determined;

$G_i$ is the weight with which the corresponding function value is multiplied;

$Sig1.Attr(i)$ is the i-th attribute of the first signature; and $Sig2.Attr(i)$ is the i-th attribute of the second signature.

In this context, depending on the data type of the two attributes between which the distance is to be ascertained, the function $DistAttr()$ can be formed as follows:

Data type string

The distance between two strings is generally used to ascertain the dissimilarity between the two strings. I.e. the more similar the two strings, the shorter the distance. For example, the distance between two strings can be calculated from the minimum number of insertion, deletion and substitution operations in order to convert one string into the other string—this is also known as the Levenshtein distance.

Data type time or time point

The distance between the time point of one signature and the time point of the other signature can be ascertained from the time interval lying between two time points. The time interval can be determined in milliseconds or days (or any other time unit) depending upon the time unit of the time points.

Data type number

The distance between two attributes of the data type number (for example integer, float) can, for example, be ascertained from the value of their difference.

Data type vector

The distance between two vectors can be determined from the Euclidean distance according to the following equation (2).

$$d = \sqrt{\sum_{i=1}^{n}(x_i - y_i)^2} \quad (2)$$

In this context, d is the Euclidean distance to be determined, $x_i$ is the i-th coordinate of the vector X of one signature and $y_i$ is the i-th coordinate of the vector Y of the other signature and n is the number of dimensions of the two vectors.

Data type property set

The distance between two property sets can, for example, be determined from the matching properties. The greater the number of matching properties, the shorter the distance.

Data type hash value

If two attributes are present in the form of hash values, the distance can be 0 if the two hash values are identical and otherwise 1.

Data type histogram

If the histogram consists of a specific number of values each indicating how frequently a specific pixel value occurs in the pixels of the image series, the amount of the differences in these values can be determined for the two signatures. In addition, the distance between two histograms can be ascertained according to the following methods known from literature: chi-square distance, Lullback-Leibler divergence, Wasserstein metric.

Data type Fourier spectrum

If a Fourier spectrum is pictured as a two-dimensional image, the pixel values of these two images of the two signatures can be subtracted pixel-by-pixel—this is also known as the Euclidean distance.

The above explicitly listed data types should be understood only as examples. According to the invention, the attributes of the signatures can also include further data types, wherein the distance or function $DistAttr()$ between these attributes can be determined according to known further elementary distance metrics.

If one attribute is not set with one signature while the corresponding attribute is set with the other signature, the distance or the function value of the function $DistAttr()$ for these attributes corresponds to the maximum value for a distance between an arbitrary value for the attribute with the one signature and an arbitrary value for the attribute with the other signature. This ensures that the distance between two set attribute values is never greater than the distance between a set attribute value and a non-set attribute value.

The set of attributes from which a signature is constructed in particular comprises so-called DICOM attributes ("digital imaging and communications in medicine") of the image series (and possibly the images) and can have at least one of following attributes:

A description of the associated image series. This description of the image series can, for example, correspond to the (in particular unique) designation of the image series. However, it is also possible for the description to be a set of keywords describing specific properties of the image series.

Scan protocol parameters of an imaging sequence with which the associated image series is to be compiled. In this context, the scan protocol parameters (for example repetition time, number of image points) define the manner in which the data for creating the image series was acquired from the examination object.

Values, which can be extracted from the pixel values or pixel data which have been reconstructed on the basis of the acquired data. These values include, for example, the following:

A histogram of the associated image series. In this context, the histogram consists of a specific number of values each indicating how frequently a specific pixel value occurs in the pixels of the image series.

A Fourier spectrum of the associated image series.

Information on anatomical landmarks or characteristics, which are visible in the associated image series. For example, the information can indicate which organs, bones, blood vessels or even lesions are visible in the respective image series.

Further possibilities for attributes of a signature are: the image type, the modality, the name of the institute, the description of the series, properties of the volume segment from which the images are created, acquisition contrast, protocol name, heart-rate synchronization technique, number of lines in the image, number of columns in the image, number of images in the image series, the administration of contrast agent for compiling the image series, etc.

The respective signature can have specific attributes of the associated image series, but it is also possible for the attributes of the signature to be derived from the attributes of the associated image series. If at least one part of the attributes of the signature is derived from the attributes of the image series, the corresponding derivation rule is in particular deterministic and reproducible.

Examples for the derivation of attributes of the signature from the attributes of an image series include the above-described histograms or Fourier spectra. The following describes further examples for the derivation of attributes of the signature from the attributes of an image series.

It is possible to calculate the difference from the two attributes 'start time point of the data acquisition' and 'end time point of the data acquisition of the image series' in order to calculate the duration of the data acquisition as an attribute of the signature.

Instead of a long string with a complete institute address, it is possible for only the hash value of this string to be stored as an attribute of the signature.

According to the invention, it is possible for the respective signature to be stored in (loss-free or lossy) compressed form or partially in the form of hash values.

According to an embodiment of the invention, a degree of similarity is determined for a similarity between the signature set of the respective segment and the signature that is ascertained as the most similar signature. In this context, this degree of similarity (or distance) determines a measure for the similarity between the signature and the respective signature set. Then, the corresponding image series is only depicted for the respective segment when the degree of similarity indicating the similarity between the signature and the signature set of the segment is above a predetermined similarity threshold. In this context, this similarity threshold can be specified individually for each segment so that each segment can have its own similarity threshold. Similarly, it is possible to define for each segment whether it is necessary to take account of the respective similarity threshold or a global similarity threshold or whether in each case the most similar image series is to be depicted, even if the degree of similarity for the respective signature is not above the similarity threshold.

This embodiment ensures that the image series depicted in a segment according to the invention has a specific similarity to the image series intended for the segment. If no image series exists with which the associated signature has a similarity to the signature set of the segment that is above the required similarity threshold, it is sometimes better not to depict an image series or an image in the segment rather than to depict a false or mismatched image series or a false or mismatched image.

According to the invention it is also possible for one or more of the segments in each case to ascertain a signature from the set of signatures of the image series that is second most similar to the signature set of the respective segment. Accordingly, the image series displayed in the respective segment is that whose signature was ascertained as second most similar.

The above-described variant enables, for example, the evaluating physician to monitor the evaluation of the image series of a specific segment using a further image series of this specific segment. While the image series of the specific segment has the most similar signature, the further image series of the specific segment has the second most similar signature.

In addition, it is also possible according to the invention for still further similar image series, for example the third most similar, fourth most similar etc., image series to be depicted in the respective segment.

Advantageously, the compilation of the signature for the respective image series can be performed during the creation of the image series by the imaging system.

Creating the signature during the creation of the image series advantageously reduces the calculation time on the actual assessment system.

According to a further preferred embodiment according to the invention, the same image series is only depicted in one of the segments.

This embodiment advantageously prevents the same image series being depicted in a plurality of segments since its signature is (randomly), for example, determined both with respect to the signature set of the first segment and with respect to the signature set of the second segment as the most similar signature. In this case, either no image series or the next most similar image series can be depicted in the corresponding segment. In other words, this embodiment advantageously ensures that another image series is displayed in each segment.

The present invention also encompasses a system for the determination of an image series from a set of a number of image series. In this context, the system has a control computer configured to use a set of attributes of the respective image series as the basis for the compilation of a signature so that the evaluation facility compiles a signature for each image series. The control computer is also configured to ascertain from the signatures of the image the signature that is most similar to a prespecified signature set and, finally, to perform an action with the image series whose signature was ascertained as the most similar signature.

The advantages of the system according to the invention correspond to the advantages of the method according to the invention for the determination of an image series from a set of a plurality of image series, which were described in detail above.

The system according to the invention can be at least one of following facilities:

A facility for medical image evaluation, which is embodied to perform as the action an image evaluation with respect to the image series whose signature was ascertained as the most similar signature.

A facility for depicting an image series in an assessment report and/or on a filming sheet, i.e. in one or more documents with which the results of an assessment are documented. In this context, the facility is embodied to depict as the action the image series in the assessment report and/or in the filming sheet whose signature was ascertained as the most similar signature.

A facility for image post-processing, which is embodied to perform as the action image post-processing with the image series whose signature was ascertained as the most similar signature.

A facility for forwarding an image series, which is embodied to perform as the action the forwarding of the image series whose signature was ascertained as the most similar signature. The selection of the image series (or the plurality of image series) that is forwarded can be performed in dependence on the object of the forwarding.

A facility for archiving an image series, which is embodied to perform as the action the archiving of the image series whose signature was ascertained as the most similar signature.

A facility for discarding, which is embodied not to perform as the action another action with respect to the image series whose signature was ascertained as the most similar signature. This entails actions which are not performed, in particular one of the actions which is performed by the above-described facilities. A system comprising the facility for discarding and one of the other facilities is then embodied such that it performs the action described with respect to the other facility for each of the image series that is not discarded.

The present invention also encompasses an imaging system for compiling a number of image series and for depicting images for evaluation by an operator. In this context, the imaging system has a computer for compiling an image series of a volume segment of an examination object and a display. The imaging system is designed to create a layout with a number of segments (or a number of layouts each with a plurality of segments) for depiction on the display in order to assign a respective signature set to each segment, in order to assign a signature to each of the plurality of image, in order to ascertain a signature from the signatures of the image series that is most similar to the signature set of the respective segment for each of the segments and in order to depict the image series in the respective segment whose signature was ascertained as most similar in the preceding step.

The imaging system can be a system for radiological evaluation, including, according to the invention, a magnetic resonance system, a computed tomography scanner, an X-ray system, a tomosynthesis apparatus, a particle-irradiation system, a positron-emission tomography scanner, a single-photon-emission computer tomography scanner, a PET-CT (combination of a positron-emission tomography scanner and a computed tomography scanner) and an mMR (combination of a positron-emission tomography scanner and a magnetic-resonance tomography scanner).

The advantages of the imaging system according to the invention correspond to the advantages of the method according to the invention for the determination of images created by an imaging system for evaluation by an operator, which were described in detail above.

The present invention also encompasses a non-transitory, computer-readable data storage medium encoded with programming instructions, the storage medium being loaded into a control computer of an imaging system and the programming instructions causing the control computer to operate the imaging system in order to implement one or more of the embodiments of the inventive method, as described above.

The program code can be a source code (for example C++) that still has to be compiled (translated) and linked or that only needs to be interpreted, or an executable software code that only needs to be loaded into the corresponding computing unit or control facility to be executed.

The electronically readable data carrier can be, for example a DVD, a magnetic tape, a hard disk or a USB stick on which electronically readable control information, in particular software (see above), is stored.

The present invention enables a workflow-based assessment also be used with a customer-specific layout without extensive configuration work.

Even when a customer's scanning programs differ greatly from a manufacturer's standard scanning programs, according to the invention, the manufacturer-configured layout can be adapted to customer-specific scanning programs very quickly. The present invention enables the typical configuration phase during which the image segments of all layouts have to be configured for the customer scanning programs to be greatly shortened.

DESCRIPTION OF THE PREFERRED EMBODIMENTS

Figure 1:
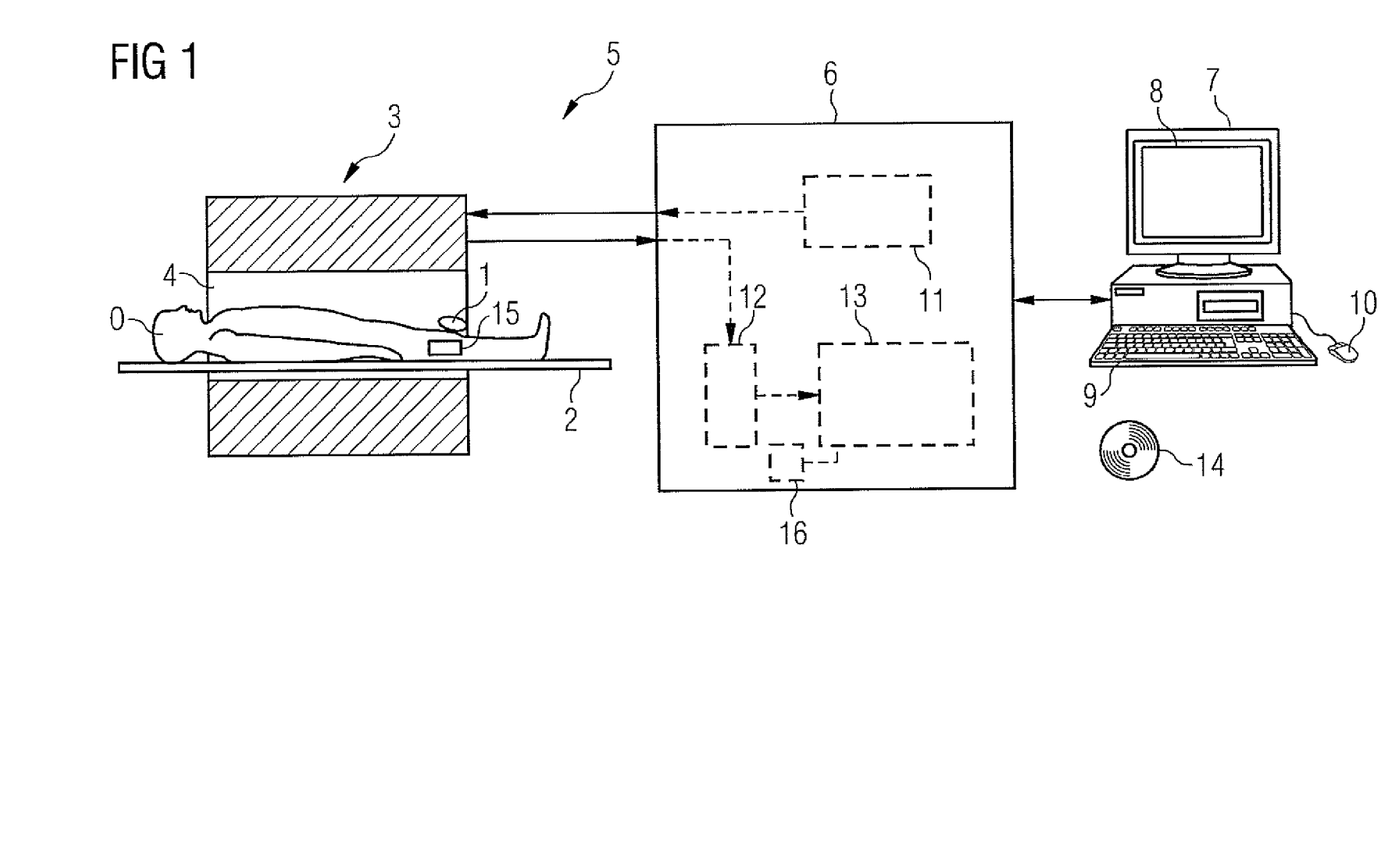
FIG. 1 is a schematic depiction of an imaging system according to the invention.

FIG. 1 is a schematic depiction of a magnetic resonance system 5 as an example of an imaging system according to the invention. The magnetic resonance system 5 has a tomography scanner 3 with which the magnetic field required for the MR examination is created in a scan chamber 4, a table or stretcher board 2, a control computer 6, with which the tomography scanner 3 is controlled and MR data are acquired by the tomography scanner 3, and a terminal 7 connected to the control computer 6.

The control computer 6 includes an actuation unit 11, a receiving apparatus 12, an evaluating apparatus 13 and a memory 16. During the compilation of an image data set, MR data is acquired by the receiving apparatus 12 by means of the tomography scanner 3, wherein the tomography scanner 3 and the table 2 are actuated by the actuation unit 11 such that that MR data are acquired in a scan volume 15 in the interior of a patient O lying on the table 2. For the compilation of a signature of an image series, the attributes of the image series can be loaded by the control computer 6 into the memory 16 in order then to form the attribute or attributes of the signature in dependence on the attributes of the image series.

The evaluating apparatus 13 then prepares the MR data such that it can be depicted graphically on a screen 8 of the terminal 7 for example in a segment of a layout. In addition to the graphical depiction of image series, the terminal 7, which in addition to the screen 8, comprises a keyboard 9 and a mouse 10, can also be used for the configuration of a layout. The software for the control computer 6 can be loaded into the control computer 6 via the terminal 7. In this context, this software in the control computer 6 can also comprise the method according to the invention. In this context, it is also possible for a method according to the invention to be contained in software that runs in the terminal 7. Regardless of which software contains the method according to the invention, the software can be stored on a DVD 14 so that this software can then be read by the terminal 7 from the DVD 14 and copied either into the control computer 6 or into a computing unit of the terminal 7 itself.

Figure 2:
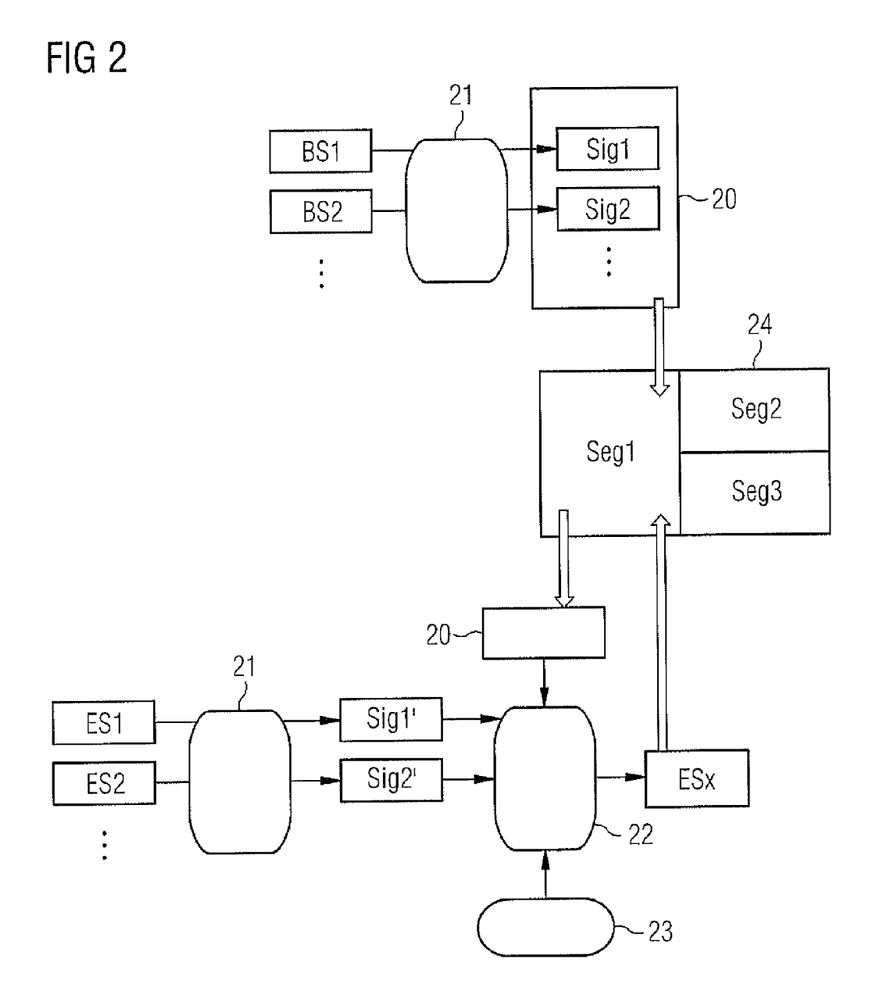
FIG. 2 is a schematic depiction of a procedure according to the invention for the determination and depiction of image series in a layout.

FIG. 2 is a schematic depiction of the procedure according to the invention for the configuration of a layout 24.

For example, a signature set or collection of signatures 20 can be compiled in a first step for each segment Seg1-3 of the layout 24. This configuration procedure can be performed at the manufacturer's premises, the customer's premises or at both the manufacturer's or customer's premises. To this end, exemplary image series BS1, BS2 are created for each segment. Then, a signature extractor 21 is used to create for each of these image series BS1, BS2a a signature Sig1, Sig2 which is stored in the associated signature set 20. The respective signature set 20 is then assigned to the corresponding segment Seg1-3 of the layout 24.

Usually, the layout 24 is configured at the manufacturer's premises, i.e. divided into corresponding segments Seg4-3 delivered to the customer. As described above, a corresponding signature set 20 is assigned to each segment Seg4-3.

For the examination of a specific examination object O, the corresponding imaging system image creates series ES1, ES2 from the examination object O. For differentiation from the above-described exemplary image series BS1, BS2, hereinafter these image series are called input image series ES1, ES2. The signature extractor 21 creates a signature Sig1 Sig2 for each of these input image series ES1, ES2.

In order to determine from each of these numerous input image, series ES1, ES2 the in each case most appropriate image series, which is depicted in one of the segments Seg1-3, each signature Sig1', Sig2' is compared by a distance metric 23 with the signature set 20 of the respective segment Seg1-3 in a comparison operation 22. For the signature Sig1', Sig2' with the shortest distance to the signature set 20, the associated input image series ESx is ascertained and then depicted as the most appropriate image series in the corresponding segment Seg1-3. This procedure is repeated for all segments Seg1-3 of the layout 24.

Figure 3:
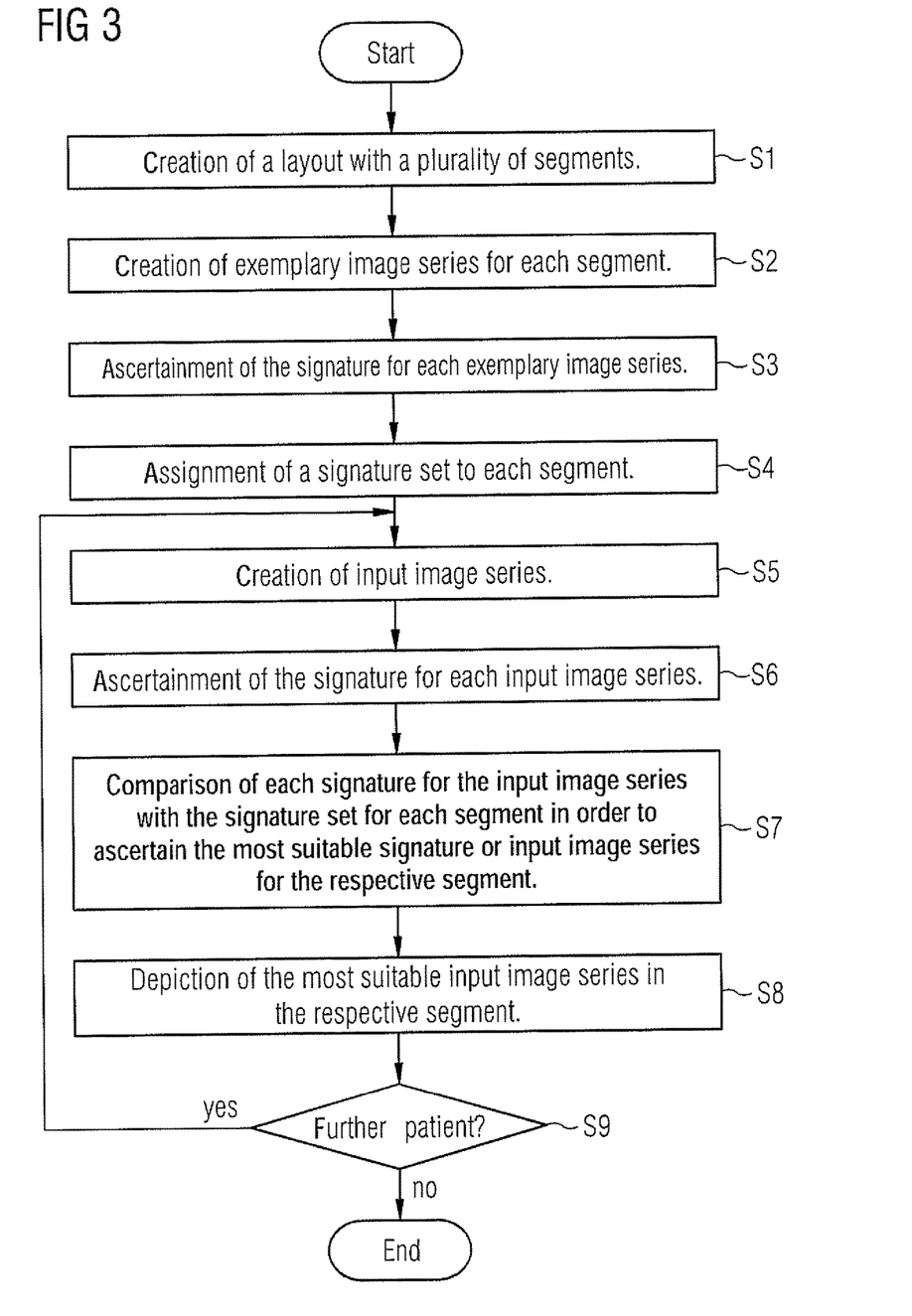
FIG. 3 is a flowchart of the method according to the invention.

FIG. 3 depicts a flowchart of the method according to the invention.

In Step S1, a layout 24 comprising a plurality of segments Seg1-3 is created. In Step S2, for each segment Seg1-3, one or more exemplary image series BS1, BS2 are created, wherein for each of these exemplary image series BS1, BS2, a signature Sig1, Sig2 is ascertained in each case in the following Step S3. In Step S4, in each case a signature set 20 is assigned to each of the segments Seg1-3. In this context, the respective signature set 20 of a segment Seg1-3 comprises the signatures Sig1, Sig2 generated for the exemplary image series BS1, BS2, which were compiled for the respective segment Seg1-3.

For the examination of a specific patient, in Step S5, an imaging system creates (for example by means of a magnetic resonance system 5) a plurality of input image series ES1, ES2. However, it is also possible according to the invention for an image series created by another system to be loaded into an assessment system (for example PACS, syngo.via) in order to examine the specific patient. In Step S6, a signature Sig1', Sig2' is now ascertained for each of these input image series ES1, ES2. In Step S7, the signatures Sig1', Sig2' of the input image series ES1, ES2 are used as the basis for the ascertainment of the signature with the shortest distance to the signature set 20 of the respective segment Seg1-3. The signature ascertained in this way is then used as the basis for the ascertainment of the associated input image series ESx, which is depicted in the respective segment Seg1-3 in Step S8.

If the question in Step S9 is answered 'yes', a further patient is examined and hence the method according to the invention returns to Step S5. If, on the other hand, the question in Step S9 is answered 'no', the method according to the invention is completed.

It is also possible to pass through a number of layouts (assessment steps) for the assessment of a patient. It is also possible for a plurality of evaluation and scan facilities to be used before the assessment of the same patient is completed.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining an image series from a set comprised of a plurality of image series, said method comprising:

generating a layout comprising a plurality of segments for depiction, at a display, in which segments of the image series in said set of a plurality of image series are to be respectively displayed;

for each image series in said plurality of image series, compiling, by a processor of a control computer, a signature from a set of attributes of that respective image series, and thereby obtaining a plurality of signatures;

assigning, by the processor, a predetermined signature set from signatures of exemplary image series to each segment of the plurality of segments of the layout;

ascertaining, by the processor, a signature among said plurality of signatures associated with the plurality of image series that is most similar to said respective assigned predetermined signature set for each segment of the plurality of segments of the layout, the ascertaining including, for each of said image series in said set of plurality of image series, determining a distance between the respective signature thereof and the predetermined signature set, and determining said most similar signature as the signature of a respective image series for which said distance is shortest, wherein each signature has the same attributes, and determining said distance as a sum of differences between attribute values of a respective signature and each signature in said predetermined signature set; and for each segment of the plurality of segments of the layout, presenting, by the processor, the image series having said most similar signature in the respective one of said segments of the layout of said display to determine a respective best match for evaluation, wherein the set of attributes includes at least one of the following attributes:

a DICOM attribute of the respective image series, values extracted from pixel values of the respective image series, a pixel value histogram of the respective image series, a Fourier spectrum of the respective image series, and information about anatomical landmarks that are visible in the respective image series.

2. A method as claimed in claim 1, wherein said distance between the respective signature thereof and the predetermined signature set is determined depending on average distances between the respective signature and each signature of the predetermined signature set.

3. A method as claimed in claim 1 wherein said distance between the respective signature thereof and the predetermined signature set is determined depending on a weighted sum distance between the respective signature and each signature of the predetermined signature set.

4. A method as claimed in claim 1 wherein determining said distance as a sum of differences between attribute values of a respective signature and each signature in said predetermined signature set.

5. A method as claimed in claim 1 comprising identifying a segment among said plurality of segments having a signature that is second most similar to said predetermined signature set, and identifying an image series having a signature that is second most similar to said predetermined image set, and displaying said image series having said second most similar signature in said segment having said second most similar signature.

6. A method as claimed in claim 1 comprising also displaying a selected image series, among said set of a plurality of image series, that does not have said most similar signature, in a different segment in said display from the segment in which said image series having the most similar signature is displayed.

7. A method as claimed in claim 1 comprising determining said distance that is shortest as an average distance that a respective image series has between all other image series in said set of a plurality of image series.

8. A method as claimed in claim 1 comprising determining said distance that is shortest as a weighted sum distance that a respective image series has between all other image series in said set of a plurality of image series.

9. A method as claimed in claim 1 wherein said distance is determined as a sum of differences between attribute values of a respective signature and each signature in said predetermined signature set.

10. A method as claimed in claim 1 wherein compiling said plurality of signatures includes compressing the respective signatures.

11. A method as claimed in claim 1 comprising determining said most similar signature by determining a degree of similarity, for each signature of each image series, to said predetermined signature set, and displaying said image series having said most similar signature only when said most similar signature has a degree of similarity that exceeds a predetermined similarity threshold.

12. A method as claimed in claim 1 comprising compiling the respective signatures of said respective image series while the respective image series is being created by an imaging system.

13. A non-transitory, computer-readable data storage medium encoded with programming instructions, said storage medium being loaded into a processor and said programming instructions causing said processor to:

generate a layout comprising a plurality of segments for depiction, at a display, in which segments of the image series in said set of a plurality of image series are to be respectively displayed;

for each image series in said plurality of image series, compile a signature from a set of attributes of that respective image series, and thereby obtaining a plurality of signatures;

assign a predetermined signature set from signatures of exemplary image series to each segment of the plurality of segments of the layout;

ascertain a signature among said plurality of signatures associated with the plurality of image series that is most similar to said respective assigned predetermined signature set for each segment of the plurality of segments, the ascertaining including, for each of said image series in said set of plurality of image series, determining a distance between the respective signature thereof and the predetermined signature set, and determining said most similar signature as the signature of a respective image series for which said distance is shortest, wherein each signature has the same attributes, and determining said distance as a sum of differences between attribute values of a respective signature and each signature in said predetermined signature set; and for each of said segments, present the image series having said most similar signature in the respective one of said segments of said display to determine a respective best match for evaluation, wherein the set of attributes includes at least one of the following attributes:

a DICOM attribute of the respective image series, values extracted from pixel values of the respective image series, a pixel value histogram of the respective image series, a Fourier spectrum of the respective image series, and information about anatomical landmarks that are visible in the respective image series.

14. An imaging system for compiling a plurality of input image series and for displaying at least one image series for evaluation, comprising:

means for compiling an input image series of a volume segment of an examination object, a control computer, and a display, wherein:

the is control computer is configured to:

create a layout comprising a plurality of segments for depiction, at at the display, in which segments of the image series in said set of a plurality of image series are to be respectively displayed;

assign a predetermined signature set from signatures of exemplary image series to each segment of the plurality of segments of the layout;

ascertain a signature among said plurality of signatures associated with the plurality of image series that is most similar to said respective assigned predetermined signature set for each segment of the plurality of segments, the ascertaining including, for each of said image series in said set of plurality of image series, determining a distance between the respective signature thereof and the predetermined signature set, and determining said most similar signature as the signature of a respective image series for which said distance is shortest, wherein each signature has the same attributes, and determining said distance as a sum of differences between attribute values of a respective signature and each signature in said predetermined signature set; and for each of said segments, present the image series having said most similar signature in the respective one of said segments on the display to determine a respective best match for evaluation, and the set of attributes includes at least one of the following attributes:
a DICOM attribute of the respective image series,
values extracted from pixel values of the respective image series,
a pixel value histogram of the respective image series,
a Fourier spectrum of the respective image series, and
information about anatomical landmarks that are visible in the respective image series.

* * * * *